US00PP12116P2

(12) United States Plant Patent
Zary

(10) Patent No.: US PP12,116 P2
(45) Date of Patent: Oct. 2, 2001

(54) FLORIBUNDA ROSE PLANT NAMED 'JACPOLPA'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/455,213

(22) Filed: Dec. 6, 1999

(51) Int. Cl.[7] ..... A01H 5/00
(52) U.S. Cl. ..... Plt./148
(58) Field of Search ..... Plt./148, 149, 137, Plt./138

*Primary Examiner*—Howard J. Locker
(74) *Attorney, Agent, or Firm*—Klarquist Sparkman Campbell Leigh & Whinston, LLP

(57) ABSTRACT

A floribunda rose plant having compact, upright growth; dark green, glossy, disease resistant foliage; and medium size pink flowers having a citrus fragrance presented in large clusters.

1 Drawing Sheet

The present invention relates to a new and distinct variety of rose plant of the floribunda class which was originated by me by crossing the variety JACship (U.S. Plant Pat. No. 7,948), with the variety JACpat (not patented).

The primary objective of this breeding was to produce a new rose variety having the vigorous, upright growth and dark green, glossy, disease resistant foliage of the female parent, combined with the compact growth, larger flowers, and large clusters of the male parent. The objective was substantially achieved, along with other desirable improvements, as evidenced by the following unique combination of characteristics that are outstanding in the new variety and that distinquish it from its parents, as well as from all other varieties of which I am aware:

1. Dark green, glossy foliage;
2. Good disease resistance;
3. Compact, upright growth;
4. Medium sized flowers presented in large clusters; and
5. Fragrance.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cutivar with color descriptions using terminology in accordance with The Royal Horticultural Society (London) colour chart, except where ordinary dictionary significance of color is indicated.

Parentage:
*Seed parent.*—JACship (U.S. Plant Pat. No. 7,948).
*Pollen parent.*—JACpat (not patented).

Classification:
*Botanical.*—*Rosa hybrida.*
*Commercial.*—Floribunda.

FLOWER

Observations made from specimens grown in a garden environment at Somis, Calif. from March 1998 to August 1999.

Blooming habit: Continuous.

Bud:
*Size.*—About 1¼ inches long when the petals start to unfurl.
*Form.*—The bud form is long; pointed ovoid.
*Color.*—When sepals first divide, bud color is Red Group 44C. When half blown, the outer ⅓ of the upper side of each petal is Red Group 48C, the inner ⅔ being Red Group 48D.
*Sepals.*—Color: Green Group 138B except when exposed to bright sun. Then they are blushed with Greyed-Purple Group 183D. Surface texture: Covered in fine hairs. There are three lightly appendaged sepals. There are two unappendaged sepals with hairy edges.
*Receptacle.*—Color: Green Group 137A. Shape: Funnel. Size: Medium (about ⅜ inch×¼ inch). Surface: Smooth.
*Peduncle.*—Length: Short (about 1½ to two inches). Surface: Glandular. Color: Green Group 137A, but when exposed to bright sun Greyed Purple Group 183A. Strength: Stiff; erect.

Bloom:
*Size.*—Medium. Average open size is 3½ inches.
*Borne.*—Several together; in rounded clusters of three to seven blooms.
*Stems.*—Strength: Strong. Average length is about 12 to 16 inches.
*Form.*—When first open: High centered. Permanence: All petals curl.
*Petalage.*—Number of petals under normal conditions: 25.
*Color.*—The outer ⅓ of the upper side of each petal is Red Group 48C, the inner ⅔ being Red Group 48D. The reverse sides of the petals are Red Group 48D. The base of each petal has on the upper surface a ⅜ inch×¼ inch Yellow Group 12B color spot, while the lower surface has a ⅛ inch×3⁄16 inch Yellow Group 3B color spot. The major color on the upper sides is Red Group 48D.
*Variegations.*—None.
*Discoloration.*—The general tonality at the end of the first day: No change. At the end of the third day: No change.
*Fragrance.*—Strong; citrus (lemon).

Petals:

*Texture.*—Thick.

*Shape.*—Round.

*Form.*—Tips slightly recurved.

*Arrangement.*—Imbricated; no petaloids in the center.

*Persistence.*—Petals drop off cleanly before drying.

*Lastingness.*—On the plant: Fair (about five days). As a cut flower: Fair (about six or seven days).

Reproductive parts:

*Anthers.*—Size: Medium. Quantity: Many. Color: Yellow-Orange Group 16D. Arrangement: Regular around styles.

*Filaments.*—Color: Yellow-Orange Group 14A.

*Pollen.*—Color: Yellow-Orange Group 22A.

*Styles.*—Color: Red Group 53C.

*Stigmas.*—Color: Yellow-White Group 159C.

Plant:

*Form.*—Bush.

*Growth.*—Vigorous; upright; branching. At maturity, height is 3½ feet, width is 2½ feet.

Foliage: Number of leaflets on normal mid-stem leaves: five or seven.

*Size.*—Large (six inches long×four inches wide).

*Quantity.*—Abundant.

*Color.*—New foliage: Upper and lower surfaces: Greyed-Purple Group 183A. Old foliage: Upper surface: Green Group 139A. Lower surface: Green Group 139C.

Leaflets:

*Shape.*—Pointed oval.

*Texture.*—Leathery; glossy.

*Edge.*—Serrated.

*Serration.*—Single; small.

*Petiole rachis.*—Color: Yellow-Green Group 147A on the upper surface, Yellow-Green Group 147C on the lower surface.

*Petiole underside.*—Rough; with prickles.

*Stipules.*—Long (about ¾ to one inch); serrated; bearded.

*Disease resistance.*—Resistant to mildew and rust, susceptible to blackspot under normal growing conditions.

Wood:

*New wood.*—Color: Greyed-Purple Group 183A. Bark: Smooth.

*Old wood.*—Color: Green Group 137A. Bark: Smooth.

Prickles:

*Quantity.*—On main canes from base: Ordinary. On laterals from main canes: Ordinary.

*Form.*—Medium; hooked slightly downward.

*Color when young.*—Greyed-Purple Group 185A.

*Color when mature.*—Greyed-Yellow Group 161A.

Small prickles:

*Quantity.*—On main stalks: None. On laterals: None.

I claim:

1. A new and distinct variety of rose plant of the floribunda class, substantially as herein shown and described, characterized particularly by having compact, upright growth; dark green, glossy, disease resistant foliage; and medium size pink flowers having a citrus fragrance presented in large clusters.

* * * * *

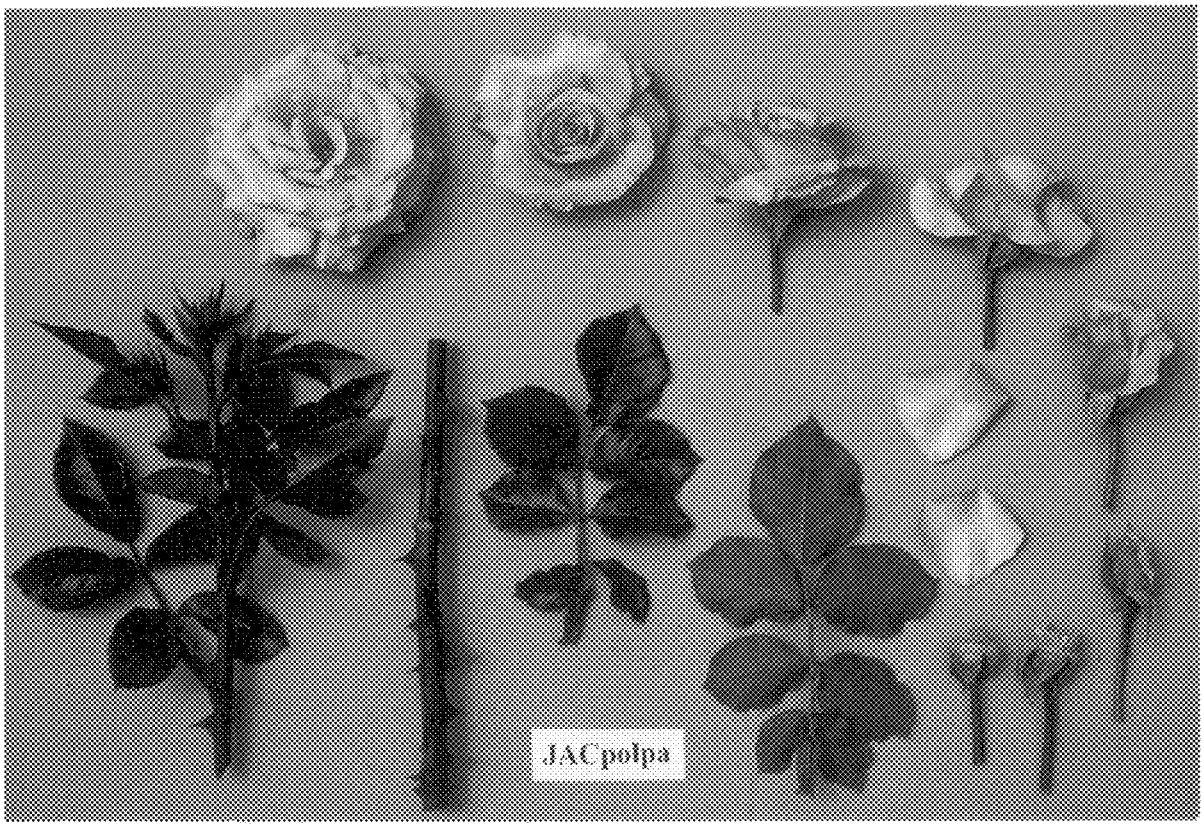
JACpolpa